United States Patent [19]

Fauss et al.

[11] Patent Number: 4,659,820

[45] Date of Patent: Apr. 21, 1987

[54] PROCESS FOR THE PREPARATION OF 4-ALKOXY-6-ALKYL-2-CYANAMINO-1,3,5-TRIAZINES

[75] Inventors: Rudolf Fauss, Cologne; Hans-Jochem Riebel, Wuppertal, both of Fed. Rep. of Germany

[73] Assignee: Bayer Aktiengesellschaft, Leverkusen, Fed. Rep. of Germany

[21] Appl. No.: 829,671

[22] Filed: Feb. 13, 1986

[30] Foreign Application Priority Data

Mar. 5, 1985 [DE] Fed. Rep. of Germany ....... 3507749

[51] Int. Cl.$^4$ .......................................... C07D 251/16
[52] U.S. Cl. .................................................. 544/194
[58] Field of Search ......................................... 544/194

[56] References Cited

FOREIGN PATENT DOCUMENTS 0121082 10/1984 European Pat. Off. .
2263853  7/1973 Fed. Rep. of Germany ...... 544/194
3334455  9/1984 Fed. Rep. of Germany .

OTHER PUBLICATIONS

Weygand/Hilgetag; Preparative Organic Chemistry (1972), p. 363, John Wiley & Sons, N.Y.

Primary Examiner—Joseph Paul Brust
Attorney, Agent, or Firm—Sprung Horn Kramer & Woods

[57] ABSTRACT

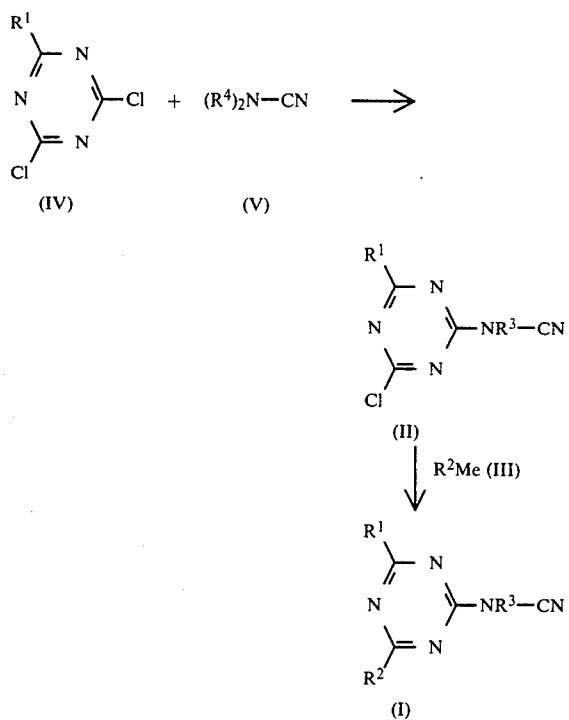

in which
  $R^1$ is alkyl,
  $R^2$ is alkoxy,
  $R^3$ is H, or one equivalent of an alkali metal or alkaline earth metal ion, and
  $R^4$ is one equivalent of an alkali metal or alkaline earth metal.

The process is new and intermediate II is new. If $R^3$ is an alkali or alkaline earth metal it can be converted to hydrogen by acid. The products are known intermediates for herbicides and plant growth regulators.

1 Claim, No Drawings

PROCESS FOR THE PREPARATION OF 4-ALKOXY-6-ALKYL-2-CYANAMINO-1,3,5-TRIAZINES

The present invention relates to new processes for the preparation of 4-alkoxy-6-alkyl-2-cyanamino-1,3,5-triazines and new intermediate products for this purpose. Some of the products of the process are known and can be used as intermediate products for the preparation of herbicides and plant growth regulators.

It is already known that 2-cyanamino-1,3,5-triazines are obtained by reacting alkali metal or alkaline earth metal salts of cyanamide with the corresponding 2-halogeno-1,3,5-triazines (see, for example, U.S. application Ser. No. 578,345, filed Feb. 9, 1984, now pending). However, because of the lack of suitable starting compounds or owing to unsatisfactory methods for the preparation of these, this process is very restricted in its use. There is therefore a need for widely applicable preparation processes for 4-alkoxy-6-alkyl-2-cyanamino-1,3,5-triazines.

It has now been found that 4-alkoxy-6-alkyl-2-cyanamino-1,3,5-triazines of the general formula (I)

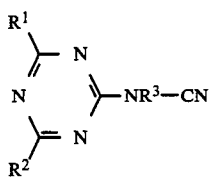

in which
R$^1$ represents alkyl,
R$^2$ represents alkoxy and
R$^3$ represents hydrogen or one equivalent of an alkali metal or alkaline earth metal ion,
are obtained if
(a) 6-alkyl-4-chloro-2-cyanamino-1,3,5-triazines of the formula (II)

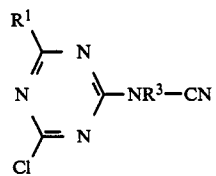

in which R$^1$ and R$^3$ have the meanings given above, are reacted with alcoholates of the formula (III)

R$^2$Me    (III)

in which
R$^2$ has the meaning given above and
Me represents an alkali metal ion, in the presence of diluents,
or if
(b) compounds of the formula (Ia), which can be prepared by the abovementioned process (a)

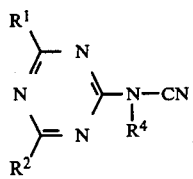

in which
R$^1$ and R$^2$ have the meanings given above and
R$^4$ represents one equivalent of an alkali metal or alkaline earth metal ion,
are converted to the compounds of the formula (Ib)

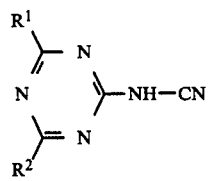

in which R$^1$ and R$^2$ have the meanings given above, in the presence of diluents and in the presence of acids.

Surprisingly, with the aid of the process according to the invention, the valuable compounds of the formula (I) can be prepared in a simple manner, in smooth reactions and in high yields, via the new intermediate products of the formula (II).

Compounds of the formula (I) which are preferably prepared with the aid of the process according to the invention are those in which
R$^1$ represents alkyl having 1 to 6 carbon atoms,
R$^2$ represents alkoxy having 1 to 6 carbon atoms and
R$^3$ represents hydrogen or one equivalent of a sodium, potassium or calcium ion.

Particularly preferably prepared compounds of the formula (I) are those in which
R$^1$ represents methyl, ethyl, n-propyl, i-propyl, n-butyl, i-butyl, sec.-butyl or tert.-butyl,
R$^2$ represents methoxy, ethoxy, n-propoxy, i-propoxy, n-butoxy, i-butoxy, sec.-butoxy or tert.-butoxy and
R$^3$ represents hydrogen or one equivalent of a sodium or potassium ion.

Very particularly preferably prepared compounds of the formula (I) are those in which
R$^1$ represents methyl, ethyl, n-propyl, i-propyl or n-butyl,
R$^2$ represents methoxy, ethoxy, n-propoxy, i-propoxy or n-butoxy and
R$^3$ represents hydrogen or one equivalent of a sodium or potassium ion.

If, for example, 4-chloro-2-cyanamino-6-methyl-1,3,5-triazine, or the corresponding sodium salt, and sodium methylate are used as starting materials for process (a) according to the invention, the reactions can be represented by the following equations:

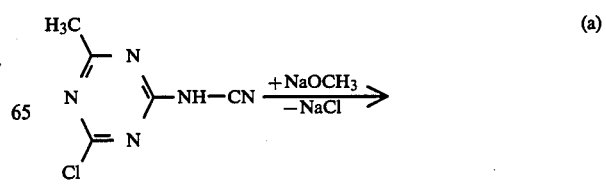

-continued

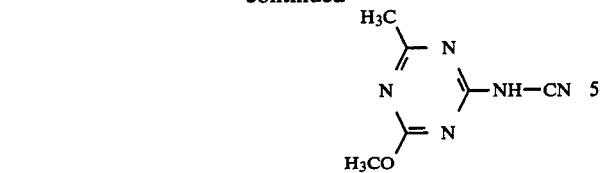

or:

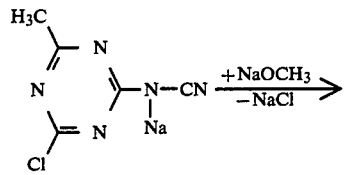

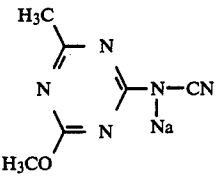

If, for example, the potassium salt of 2-cyanamino-6-methyl-4-ethoxy-1,3,5-triazine is used as a starting material and hydrochloric acid is used as the mineral acid for process (b) according to the invention, the reaction can be represented by the following equation:

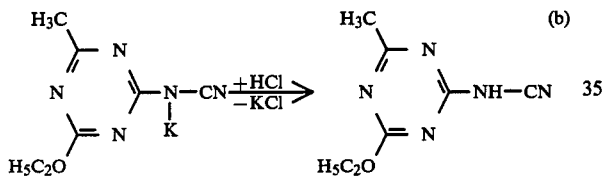

Formula (II) gives a general definition of the 6-alkyl-4-chloro-2-cyanamino-1,3,5-triazines to be used as starting materials for process (a) according to the invention. Preferred compounds of the formula (II) are those in which $R^1$ represents alkyl having 1 to 6 carbon atoms and
$R^3$ represents hydrogen or one equivalent of a sodium, potassium or calcium ion.

Particularly preferred compounds of the formula (II) are those in which $R^1$ represents methyl, ethyl, n-propyl, i-propyl, n-butyl, i-butyl, sec.-butyl or tert.-butyl and
$R^3$ represents hydrogen or one equivalent of a sodium or potassium ion.

Very particularly preferred compounds of the formula (II) are those in which $R^1$ represents methyl, ethyl, n-propyl, i-propyl or n-butyl and
$R^3$ represents hydrogen or one equivlent of a sodium or potassium ion.

The following may be mentioned as examples of the starting materials of the formula (II): 6-methyl-, 6-ethyl-, 6-n-propyl-, 6-i-propyl-, 6-n-butyl-, 6-i-butyl-, 6-sec.-butyl- and 6-tert. butyl-4-chloro-2-cyanoamino-1,3,5-triazine and the corresponding sodium and potassium salts.

The compounds of the formula (II) are new. The compounds of the formula (II) are obtained if 2,4-dichloro-6-alkyl-1,3,5-triazines of the formula (IV)

in which $R^1$ has the meaning given above, are reacted with cyanamides of the formula (V)

$$(R^4)_2N-CN \tag{V}$$

in which $R^4$ has the meaning given above, in the presence of water, at a pH value of between 8.5 and 9.5 and at temperatures between −5° C. and +10° C., to give the compounds of the formula (IIa)

in which $R^1$ and $R^4$ have the meanings given above, and, if required, these compounds of the formula (IIa), if appropriate after they have been isolated, are then converted to the compounds of the formula (IIb)

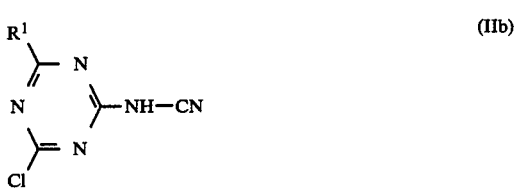

in which $R^1$ has the meaning given above, in the presence of water and in the presence of acids, such as, for example, hydrochloric acid, at temperatures between −10° C. and +20° C.

Formula (IV) gives a general definition of the 2,4-dichloro-6-alkyl-1,3,5-triazines to be used as starting materials for the preparation of the compounds of the formula (IIa) or (IIb). In this formula, $R^1$ preferably represents those radicals which have been mentioned in the context of the definition of the substituents of the formula (II) as being preferred or as being particularly preferred.

The following may be mentioned as examples of the compounds of the formula (IV): 6-methyl-, 6-ethyl-, 6-n-propyl-, 6-i-propyl-, 6-n-butyl-, 6-i-butyl-, 6-sec.-bityl- and 6-tert.-butyl-2,4-dichloro-1,3,5-triazine.

The compounds of the formula (IV) are known (see, for example, Helv. Chim. Acta 33, 1365 (1950)).

Formula (V) gives a general definition of the cyanamides furthermore to be used as starting materials for the preparation of the compounds of the formula (IIa) or (IIb). In this formula, $R^4$ preferably represents one equivalent of a sodium, potassium or calcium ion.

The following may be mentioned as examples of the compounds of the formula (V): Di-sodium cyanamide, di-potassium cyanamide and calcium cyanamide.

The compounds of the formula (V) are generally known compounds of organic chemistry.

Formula (III) gives a general definition of the alcoholates furthermore to be used as starting materials for process (a) according to the invention. In this formula, R² preferably has those meanings which have been mentioned above in the context of the definition of the substituents of the formula (I) as being preferred or as being particularly preferred. In this formula, Me preferably represents a sodium or potassium ion.

The following may be mentioned as examples of the compounds of the formula (III): Sodium methylate, ethylate, n-propylate, i-propylate, n-butylate, i-butylate, sec.-butylate and tert.-butylate and the corresponding potassium derivatives.

The compounds of the formula (III) are generally known compounds of organic chemistry.

Process (a) according to the invention is carried out in the presence of diluents.

These include, in particular, aliphatic and aromatic hydrocarbons, such as pentane, hexane, heptane, cyclohexane, petroleum ether, benzine, ligroin, benzene, toluene, xylene, and alcohols, such as methanol, ethanol, n-propanol, i-propanol, n-butanol, i-butanol, sec.-butanol and tert.-butanol. The corresponding alcohols of the alcoholates of the formula (III) employed are preferably used.

Process (a) according to the invention is carried out in general at temperatures between 0° C. and 50° C., preferably about 0° C. and 40° C. The reactions are carried out in general under atmospheric pressure.

In carrying out process (a) according to the invention, 1.0 to 1.4 mols, preferably 1 to 1.2 mols, of the alcoholate of the formula (III) are employed per mol of the compound of the formula (IIa), or 2.0 to 2.5 mols, preferably 2.0 to 2.3 mol, of the alcoholate of the formula (III) are employed per mol of the compound of the formula (IIb). The compounds of the formula (I) are worked up by customary methods. When the addition of the starting materials is complete, stirring is continued for a short time or for several hours at 15° C. to 25° C. Thereafter, where compounds of the formula (Ia) are being prepared, the mixture is, if appropriate, diluted with alcohol and evaporated down in vacuo at temperatures below 50° C., and where compounds of the formula (Ib) are being prepared, water is added and the mixture is acidified with a mineral acid, such as, for example, hydrochloric acid. The compounds of the formula (I) are obtained in general in crystalline form.

Formula (Ia) gives a general definition of the compounds to be used as starting materials for process (b) according to the invention. In this formula, R¹ and R² represent those radicals which have been mentioned above in the context of the definition of the substituents of the formula (I) as being preferred or as being particularly preferred. In this formula R⁴ preferably represents one equivalent of a sodium, potassium or calcium ion.

The following may be mentioned as examples of the compounds of the formula (Ia): The sodium, potassium and calcium salts of 6-methyl-4-methoxy-, 6-methyl-4-ethoxy-, 6-methyl-4-n-propoxy-, 6-methyl-4-i-propoxy-, 6-methyl-4-n-butoxy-, 6-methyl-4-i-butoxy-, 6-methyl-4-sec.-butoxy-, 6-methyl-4-tert.-butoxy-, 6-ethyl-4-methoxy-, 6-ethyl-4-ethoxy-, 6-ethyl-4-n-propoxy-, 6-ethyl-4-i-propoxy-, 6-ethyl-4-n-butoxy-, 6-ethyl-4-i-butoxy-, 6-ethyl-4-sec.-butoxy-, 6-ethyl-4-tert.-butoxy-, 6-n-propyl-4-methoxy-, 6-n-propyl-4-ethoxy-, 6-n-propyl-4-n-propyl-, 6-n-propyl-4-n-propoxy-, 6-n-propyl-4-n-butoxy-, 6-n-propyl-4-i-butoxy-, 6-n-propyl-4-sec.-butoxy-, 6-n-propyl-4-tert.-butoxy-, 6-i-propyl-4-methoxy-, 6-i-propyl-4-ethoxy-, 6-i-propyl-4-n-propoxy-, 6-i-propyl-4-i-propoxy-, 6-i-propyl-4-n-butoxy-, 6-i-propyl-4-i-butoxy, 6-i-propyl-4-sec.-butoxy-, 6-i-propyl-4-tert.-butoxy-, 6-n-butyl-4-methoxy-, 6-n-butyl-4-ethoxy-, 6-n-butyl-4-n-propoxy-, 6-n-butyl-4-i-propoxy-, 6-n-butyl-4-n-butoxy-, 6-n-butyl-4-i-butoxy-, 6-n-butyl-4-sec.-butoxy-, 6-n-butyl-4-tert.-butoxy-, 6-i-butyl-4-methoxy-, 6-i-butyl-4-ethoxy-, 6-i-butyl-4-n-propoxy-, 6-i-butyl-4-i-propoxy-, 6-i-butyl-4-n-butoxy-, 6-i-butyl-4-i-butoxy-, 6-i-butyl-4-sec.-butoxy-, 6-i-butyl-4-tert.-butoxy-, 6-sec.-butyl-4-methoxy-, 6-sec.-butyl-4-ethoxy-, 6-sec.-butyl-4-n-propoxy-, 6-sec.-butyl-4-i-propoxy-, 6-sec.-butyl-4-n-butoxy-, 6-sec.-butyl-4-i-butoxy-, 6-sec.-butyl-4-sec.-butoxy-, 6-sec.-butyl-4-tert.-butoxy-, 6-tert.-butyl-4-methoxy-, 6-tert.-butyl-4-ethoxy-, 6-tert.-butyl-4-n-propoxy-, 6-tert.-butyl-4-i-propoxy-, 6-tert.-butyl-4-n-butoxy-, 6-tert.-butyl-4-i-butoxy-, 6-tert.-butyl-4-sec.-butoxy- and 6-tert.-butyl-4-tert.-butoxy-2-cyanamino-1,3,5-triazine.

The compounds of the formula (Ia) can be prepared by process (a) according to the invention.

Process (b) according to the invention is preferably carried out in the presence of water as a diluent.

Process (b) according to the invention is carried out in the presence of acids. Hydrochloric acid, hydrobromic acid, sulphuric acid, phosphoric acid and acetic acid have proven particularly useful. Hydrochloric acid is preferably used.

Process (b) according to the invention is carried out in general at temperatures between −10° C. and +25° C., preferably between −5° C. and +20° C. The reactions are carried out in general under atmospheric pressure. In carrying out process (b) according to the invention, 1 to 3 mols, preferably 1.8 to 2.3 mols, of the acid are employed per mol of the compound of the formula (Ia). Working-up is carried out by customary methods.

The 4-alkoxy-6-alkyl-2-cyanamino-1,3,5-triazines to be prepared by the process according to the invention can be employed as intermediate products for the preparation of guanidine derivatives, which are effective as herbicides and plant growth regulators (see EP-OS (European Published Specification) No. 121,082).

PREPARATION EXAMPLES

Example 1

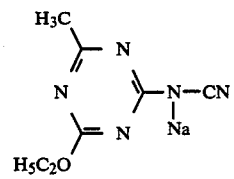

(Process (a))

A solution of 3.7 g (0.16 mol) of sodium in 100 ml of ethanol is added dropwise to a solution of 29 g (0.15 mol) of the sodium salt of 4-chloro-2-cyanamino-6-methyl-1,3,5-triazine in 500 ml of ethanol in a manner such that a reaction temperature of 30° C. is not exceeded. Thereafter, the mixture is stirred for a further 3 hours at 20° C., diluted with 400 ml of ethanol and filtered. The filtrate is evaporated down in vacuo, the temperature not exceeding 45° C.

29.9 g (99% of theory) of the sodium salt of 2-cyanamino-4-ethoxy-6-methyl-1,3,5-triazine of melting point 200° C. (decomposition) are obtained in this manner.

Example 2

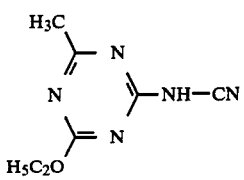

(Process (a))

8.5 g (0.05 mol) of 4-chloro-2-cyanamino-6-methyl-1,3,5-triazine are added in portions to a solution of 2.5 g (0.11 mol) of sodium in 100 ml of ethanol in a manner such that a temperature of 35° C. is not exceeded. Thereafter, the miture is stirred for a further hour at 20° C. and evaporated down in vacuo in a manner such that a bath temperature of 50° C. is not exceeded. The residue is dissolved in 50 ml of water, and the solution is acidified with 6 ml of concentrated hydrochloric acid. The resulting crystals are filtered off under suction and dried.

8.1 g (91% of theory) of 2-cyanamino-4-ethoxy-6-methyl-1,3,5-triazine of melting point 195° C. (decomposition) are obtained.

Example 3

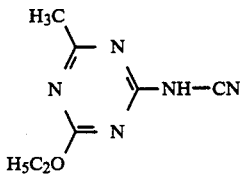

(Process (b))

50 ml of 20% strength hydrochloric acid are added to a solution of 30.1 g (0.15 mol) of the sodium salt of 2-cyanamino-4-ethoxy-6-methyl-1,3,5-triazine in 300 ml of water at 0° C. to 10° C., and the mixture is stirred for a further 15 minutes at 10° C. The precipitate is filtered off under suction and dried.

26.5 g (98% of theory) of 2-cyanamino-4-ethoxy-6-methyl-1,3,5-triazine of melting point 195° C. (decomposition) are obtained.

The following compounds can be prepared analogously to Example 1 to 3 and processes (a) and (b):

Example 4

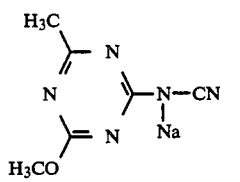

m.p.: 220° C. (decomposition)

Example 5

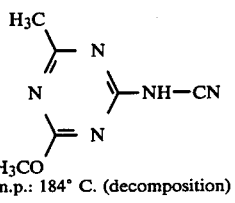

m.p.: 184° C. (decomposition)

PREPARATION OF STARTING MATERIALS OF THE FORMULA (II)

Example (II-1)

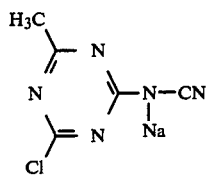

4.5 g (0.05 mol) of di-sodium cyanamide in 50 ml of water are added dropwise, at a temperature of 0° C. to 5° C., to a suspension of 8.2 g (0.05 mol) of 2,4-dichloro-6-methyl-1,3,5-triazine in 100 ml of ice water in a manner such that a pH value of 9.5 is not exceeded. Thereafter, the mixture is stirred for a further hour at 20° C., 40 g of sodium chloride are added and stirring is continued for about 0.5 to 1 hour at 20° C.

After the product has been filtered off under suction and dried, 9.1 g (95% of theory) of the sodium salt of 4-chloro-2-cyanamino-6-methyl-1,3,5-triazine of melting point 190° C. (decomposition) are obtained.

Example (II-2)

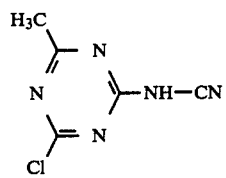

1 ml of concentrated hydrochloric acid is added to a suspension of 2 g (0.01 mol) of the sodium salt of 4-chloro-2-cyanamino-6-methyl-1,3,5-triazine in 50 ml of water at 0° C. to 10° C. The resulting precipitate is filtered off under suction and dried.

1.3 g (77% of theory) of 4-chloro-2-cyanamino-6-methyl-1,3,5-triazine of melting point 105° C. (decomposition) are obtained in this manner.

It will be understood that the specification and examples are illustrative but not limitative of the present invention and that other embodiments within the spirit and scope of the invention will suggest themselves to those skilled in the art.

What is claimed:

1. A 6-alkyl-4-chloro-2-cyanamido-1,3,5-triazine of the formula

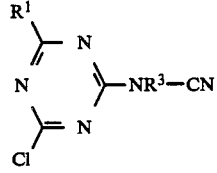

in which
$R^1$ is $C_1$-$C_6$-alkyl, and
$R^3$ is hydrogen, Na, K or one equivalent of Ca.

* * * * *